(12) United States Patent
Adams et al.

(10) Patent No.: US 7,435,407 B2
(45) Date of Patent: *Oct. 14, 2008

(54) INHIBITION OF OLFACTORY NEUROSENSORY FUNCTION TO TREAT EATING DISORDERS AND OBESITY

(75) Inventors: Christopher P. Adams, Somerville, MA (US); James Flynn, Lexington, MA (US)

(73) Assignee: Compellis Pharmaceuticals, Somerville, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/528,978

(22) Filed: Sep. 27, 2006

(65) Prior Publication Data
US 2007/0025921 A1    Feb. 1, 2007

Related U.S. Application Data

(63) Continuation of application No. 10/369,188, filed on Feb. 18, 2003, now Pat. No. 7,138,107.

(60) Provisional application No. 60/431,265, filed on Dec. 9, 2002.

(51) Int. Cl.
*A61K 9/12* (2006.01)
*A61K 9/14* (2006.01)
*A61K 31/47* (2006.01)

(52) U.S. Cl. .......................... 424/45; 424/46; 424/434; 424/489; 514/909; 514/866

(58) Field of Classification Search ................ 424/45, 424/46, 434, 489; 514/909, 866
See application file for complete search history.

(56) References Cited

U.S. PATENT DOCUMENTS

| 4,605,552 A | 8/1986 | Fritschi .................. 424/45 |
| 6,100,047 A | 8/2000 | Wilkison et al. |
| 7,138,107 B2 * | 11/2006 | Adams et al. ............. 424/45 |
| 2003/0032595 A1 | 2/2003 | Desir et al. |

OTHER PUBLICATIONS

Watt, W.C. and Storms, D.R., J. Biol. Chem., 2001; 276(1):2047-2052.
Wong et al., Neuron, 2000; 27:487-97.

* cited by examiner

*Primary Examiner*—Mina Haghighatian
(74) *Attorney, Agent, or Firm*—Darby & Darby P.C.

(57) ABSTRACT

The use of calcium channel blockers administered intra-nasally to inhibit olfactory sensory perception to treat eating disorders, including obesity, is described. Also described is a method of reducing food intake in a subject by administering a pharmaceutical composition comprising an effective amount of a calcium channel blocker to the nasal mucosa, as well as screening methods for drugs to be used in treating obesity or associated disorders.

17 Claims, 4 Drawing Sheets

INHIBITION OF OLFACTORY NEUROSENSORY FUNCTION TO TREAT EATING DISORDERS AND OBESITY

This application is a continuation of U.S. patent application Ser. No. 10/369,188, filed Feb. 18, 2003, which claims priority under 35 U.S.C. § 119(e) to U.S. Provisional Application No. 60/431,265, filed Dec. 9, 2002, the entire disclosures of which are hereby incorporated by reference.

FIELD OF THE INVENTION

This invention relates to the inhibition of olfactory neurosensory perception and methods to treat eating disorders.

BACKGROUND OF THE INVENTION

Olfactory Perception

Olfactory perception is well understood biologically. Specialized cells are organized in the nose to bind various classes of odorants and transduce a signal to the brain to interpret the smell. The signal involves odorant binding factors, olfactory receptor neurons and surrounding cells in the nasal mucosa, the olfactory nerve, the olfactory bulb, and connections to the limbic region of the brain.

Olfactory receptor neurons are embedded in the nasal epithelium, which contains olfactory receptors embedded in plasma membrane that bind odorants. The intracellular signal transduction machinery couples the olfactory receptors to heterotrimeric G-proteins. Odorant binding to the extracellular domains stimulates the intracellular domain to initiate the G-protein cascade. G-protein couples cell-surface receptors to the activation of adenylyl cyclases and cyclic AMP (cAMP) production. Cyclic nucleotide-gated (CNG) channels are subsequently activated by cAMP binding and open to allow an influx of calcium ($Ca^{++}$). $Ca^{++}$-activated chloride ion channels in the plasma membrane then open and conduct a depolarizing receptor current that leads to electrical excitation of the neuron.

In olfactory receptor neurons, much of the depolarizing current in response to odors is carried by cationic channels that are directly gated by cyclic AMP. Cyclic nucleotide-gated channels comprise a family of proteins. The family has been well studied and molecular modulators have been identified.

Obesity

Being obese and being overweight, although closely related, are not the same condition. Body Mass Index, or BMI, is a mathematical calculation used to determine whether a patient is overweight. BMI is calculated by dividing a person's body weight in kilograms by their height in meters squared (weight (kg)/height (m)$^2$) or by using the conversion with pounds and inches squared (weight (lbs)/height (in)$^2$×704.5). A BMI of 30 or greater is considered obese and a BMI between 25-29.9 is considered overweight (National Institutes of Health, National Heart Lung and Blood Institute: Clinical Guidelines on the Identification, Evaluation, and Treatment of Overweight and Obesity in Adults. June 1998).

The number of overweight and obese Americans has continued to increase since 1960, a trend that is not slowing down. Today, 55% of adult Americans (97 million) are categorized as being overweight or obese. The prevalence of obesity is rising dramatically, a trend that has accelerated over the last decade, and is rapidly becoming an epidemic of global proportions. By 2008 over 60% of the US population is expected to be clinically overweight, while in Europe (the United Kingdom, Germany, France, Italy and Spain) an average of 50% of people will be overweight. Right now, at least 39 million Americans: more than one-quarter of all adults and about one in five children. Some people are more susceptible to obesity than others. Each year, obesity causes at least 300,000 excess deaths in the U.S. and costs the country more than $100 billion. Developing nations are also dramatically affected, creating a significant burden on healthcare services. The rapid increase in the prevalence of obesity is strongly linked to changing lifestyles, which have seen an increase in the consumption of energy dense food associated with a decrease in physical activity. Of increasing concern is the effect these changes are having on the child and adolescent populations. Recent studies have shown that adolescent obesity is becoming increasingly prevalent, and as obese children are more likely to become obese adults, these changes will have a major impact on the health of the adult population in 10-20 years.

Obesity is a chronic disease linked to a number of serious co-morbidities, associated not only with a social stigma, but also with decreased life span and numerous medical problems, including adverse psychological development, reproductive disorders such as polycystic ovarian disease, dermatological disorders such as infections, varicose veins, Acanthosis nigricans, and eczema, exercise intolerance, type II diabetes mellitus, insulin resistance, hypercholesterolemia, cholelithiasis, osteoarthritis, orthopedic injury, thromboembolic disease, cancer, coronary heart disease, cardiovascular disease, artherosclerosis, and hypertension (Rissanen et al., British Medical Journal, 301: 835-837 (1990)). Preventing and reversing obesity has a positive impact on reducing these complications.

The pathogenesis of obesity is multi-factorial and includes the control of feeding behavior, mechanisms of fat storage, the components of energy intake and expenditure, and genetic and psychological influences. Likewise, the treatment regimen for reversing obesity is generally multi-factorial. However, most clinically supported approaches report small and non-lasting effects of weight loss. Targeting the mechanisms of lipid metabolism and fat storage or understanding complex genetic influences have not provided adequate results. Moreover, the control of feeding behavior, exercise and psychological influences has produced positive results. Although the individual components of energy intake and expenditure are treatable, many obese individuals are resistant to or incapable of engaging in activities that significantly increase their energy expenditure. Therefore, controlling energy intake by suppressing appetite is an attractive approach for the treatment of obesity. Combining appetite suppression in its earliest stages of olfactory perception and feeding behavior with other methods of weight reduction can produce better clinical outcomes.

Natural and synthetic substances are known to positively modulate and reverse the effects of physiological disorders, like obesity. See, e.g., Arner, Int J Obes (1993) 17 (Suppl. 1), S57-S59; Astrup et al., Am J Clin Nutr (1990) 51:759-67; and Astrup et al., Int J Obes (1992) 16:269-277. Such substances act by a variety of mechanisms. For example, some substances act by mimicking the effects of endogenous neurotransmitters, and are capable of directly replacing these neurotransmitters in their actions on receptors. This, in turn, leads to increased activity of the cells that possess the receptors. Where the receptors concerned are normally responsive to the endogenous hormones adrenaline (epinephrine) and noradrenaline (norepinephrine), which mediate the activities of the sympathetic nervous system, such substances are termed direct-acting sympathicomimetic agents. Typical examples are the amphetamines. Other substances that produce similar effects on the sympathetic nervous system do so by stimulating the release of the endogenous hormones adrenaline and noradrenaline, and are thus termed indirect-acting sympathicomimetic agents. Ephedrine is a typical example of an indirect-acting sympathicomimetic agent. The term adrenergic may also be used, and is synonymous with the term sympathicomimetic. Such substances may also be referred to as agonists, where the name agonist is qualified by a descriptor of the receptor stimulated, for example, a beta-agonist.

Another class of substances modulates other neurotransmitters, namely those involved in serotoninergic systems, and particularly 5-hydroxytryptamine (otherwise known as 5-HT or serotonin) itself. These substances, of which fenfluramine and its optical isomer, dexfenfluramine, are typical, act by preventing the re-uptake of serotonin into storage granules in neurones. Levels of 5-HT in the synaptic gap thus remain elevated for longer periods, exciting receptors on responsive cells to greater activity. Substances that act by increasing the availability of 5-hydroxytryptamnine are known to increase perceptions of satiety.

Substances which modulate neurotransmitter function in the central nervous system are known to act by increasing the availability of catecholamines, in particular noradrenaline, in certain areas of the brain, thus resulting in perceived suppression of hunger. By suppressing hunger, less food is eaten, and caloric intake is lowered. Examples of such substances include phenylpropanolamine, phentermine and the amphetamines.

Irrespective of mechanism, substances of either of these types result in reduced food intake. But their use can be attended by various unwanted effects characteristic of interference with other hormone-regulated systems in the body. Furthermore tachyphylaxis has been noted where the effects of these types of substances are transient, requiring progressively greater dosage to elicit desired effects, until the body finally becomes unresponsive.

Other aids to weight loss have been proposed, such as substances which prevent the absorption of nutrients from the digestive system, but the value of such approaches is minimal, and in general, the accepted substances of value in weight loss act by modulating neurotransmitter function in the central nervous system or peripherally. The most severe treatment has involved radical surgery, with removal of a major portion of the digestive tract.

Thus, despite advances in the art, there is a need for safe and effective methods to treat eating disorders, obesity, and associated physiological disorders. The present invention addresses these and other needs in the art.

SUMMARY OF THE INVENTION

According to the invention, physiological disorders associated with eating habits can be treated or prevented by modulating the sense of smell or taste. For example, compositions comprising calcium channel agonists or antagonists can be used to treat eating disorders, obesity, and associated physiological disorders. Without being bound to any specific theory, by contacting nasal mucosa or olfactory tissue comprising olfactory receptor neurons with such compositions, signal transduction pathways specific for the functions of smell or taste are triggered, resulting in modulation of food intake.

Thus, the invention provides, a method of reducing food intake in a subject in need thereof, comprising the step of administering a pharmaceutical composition comprising an effective amount of a calcium channel blocker to nasal mucosa of a subject. In one embodiment, the subject suffers from obesity or a physiological disorder associated with obesity. The physiological disorder can be a member of the group consisting of atherosclerosis, coronary artery disease, hypertension, hypercholesterolemia, diabetes mellitus, gout, osteoarthritis, intertrigo, sleep apnea, hyperlipidemia, hypolipidemia, hypoproteinemia, Pickwickian syndrome, and Cushing syndrome. The pharmaceutical composition can be, for example, in the form of a liquid. In this embodiment, the administering is advantageously in the form of inhalation or topical administration. The calcium channel blocker includes, but is not limited to, a member of the group consisting of diltiazem, verapamil, fluoxetine, nifedipine, nimodipine, amlodipine, felodipine, nicardipine, bepridil and nisoldipine. Preferably, the calcium channel blocker is diltiazem, verapamil, amlodipine, nimodipine, or isradipine, or a combination thereof. Most preferably, the calcium channel blocker is diltiazem. The pharmaceutical composition may, for example, comprise from about 0.5 to about 30 mg diltiazem, preferably from about 1 to about 20 mg diltiazem. The administering can be made from about 0.5 to about 12 hours before food intake, preferably from about 1 to about 2 hours before food intake. In one embodiment, the pharmaceutical composition is administered at least once daily for at least 2 days. In another embodiment, the pharmaceutical composition is administered twice daily.

The invention also provides a method of screening to identify an agent useful for treating or preventing obesity which comprises (i) providing a pool of test agents; (ii) determining whether any test agent from the pool is an antagonist of a cyclic-nucleotide-gated (CNG) calcium channel specific for olfactory neurons; and (iii) selecting any test agent from the pool that is an antagonist as an agent useful for treating or preventing obesity. The method can also comprise a step of selecting the pool of test agents prior to step (i).

The invention also provides a method of treating or preventing obesity, comprising the step of administering a pharmaceutical composition comprising an effective amount of diltiazem to nasal mucosa of a subject suffering from or at risk for obesity. Preferably, the pharmaceutical composition comprises from about 0.5 to about 30 mg diltiazem, more preferably from about 1 to about 20 mg diltiazem. The administering is preferably made from about 1 to about 2 hours before food intake.

DETAILED DESCRIPTION OF THE INVENTION

Figure 1:
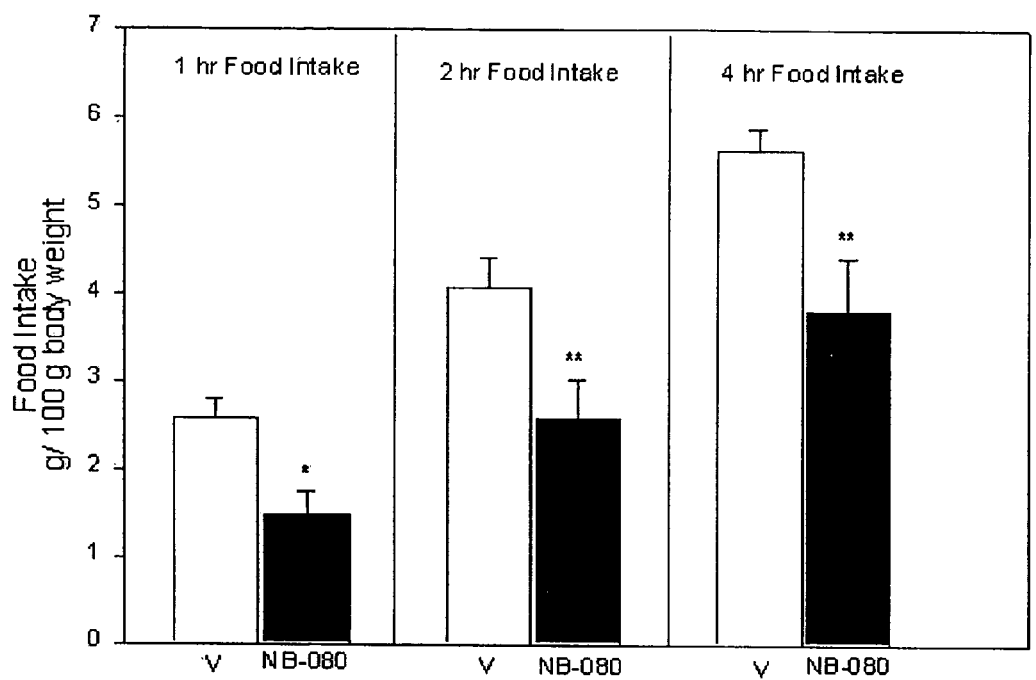
FIG. 1. Effect of intranasal diltiazem (NB-080; 20 µL per nostril) on food intake in food-deprived rat. Food was given to the animals one hour after drug administration. V=Vehicle (control). *=Statistically significant difference from vehicle-treated group, $p<0.01$. **=Statistically significant difference from vehicle-treated group, $p<0.05$.

The present invention is based, in part, on the identification of calcium channels, more specifically calcium channels associated with activation of olfactory perception, as drug targets for modulating food intake. For example, a calcium channel blocker can be administered intra-nasally to inhibit olfactory sensory perception, thereby promoting a patient suffering from obesity or an associated disorder to reduce food intake. Calcium channel blockers can inhibit the cyclic nucleotide gated channel in the olfactory epithelium, thereby targeting the biochemical entities involved in signal transduction pathways specific for the functions of smell. Thus, according to the invention, the administration of a calcium channel blocker reducing or eliminating olfactory sensory perception will reduce food consumption in mammals. A preferred, although non-limiting, calcium channel blocker according to the invention is diltiazem. As described in the Examples, intranasal administration of diltiazem resulted in decreased food intake in an animal model.

Preferably, the calcium channel blocker is administered topically on nasal mucosa by way of an aerosol spray or nose drops. In one embodiment, the composition is administered prior to food intake, preferably 0.5 to 4 hours prior to food intake, more preferably 1 to 2 hours before food intake. In another embodiment, the administration of calcium channel blocker is repeated at intervals and for a period time as required to maintain a desired level of activity, or to achieve the desired weight loss. For example, a patient may self-administer a 2 mg dose of diltiazem intra-nasally twice daily. The expected duration of such therapy can range from 1 day to 12 months, preferably from 6 to 12 months. The duration of the treatment period ultimately depends on the patient's physical condition or weight status, and the desired outcome of the therapy.

The methods of the invention can modulate the sense of smell to treat eating disorders, obesity, or physiological disorders associated with such conditions. Taste, or gustatory perception, is controlled about two-thirds by smell, olfactory perception. For this reason, the methods for modulating the sense of smell to treat physiological disorders can effectively modulate taste. The pharmaceutical compositions used in the methods of the invention comprise compounds that block calcium channel function in olfactory perception. Thus, without being bound to any theory, the treatment regimen results in a decrease in food consumption and the caloric intake due to the absence of food related environmental cues and the flavors associated with eating and tasting food. This drug therapy can be used by those who have a desire to eat less and are effected by overeating, binges and or cravings.

The methods of treatment described can directly affect limbic brain responses through the nervous system because there is only one synaptic junction between olfactory receptor neurons and the limbic region of the brain. Because sensory nerves are addressed to a specific location in the brain, targeting olfactory neuron calcium channels can have a highly specific drug effect, thereby greatly reducing the potential of undesirable side effects.

Thus, in one embodiment of the present invention, olfactory perception is modulated in animals by contacting nasal mucosa or olfactory tissue with modulator molecules that block cyclic nucleotide gated calcium channels, thus resulting in decreased food intake.

In another embodiment, the modulator molecules are delivered in a non-systemic format by administration to the nasal mucosa. This particular mode of administration is distinguished from alternative modes, such as ingestion or injection, in several important ways, by virtue of the direct contact with the olfactory receptor neurons provided by the nasal administration of the modulators.

The present invention also provides methods to identify compounds or compositions to treat eating disorders, obesity, or related physiological disorders. According to this embodiment, in vitro or in vivo screening assays are used to identify agents that are antagonists of a CNG calcium channel specific for olfactory neurons. In one embodiment, the screening method comprises measuring calcium influx into cultured cells, e.g., olfactory receptor neurons, in the presence and absence of test agents. For example, the cells can be contacted with a stimulus for calcium influx, and a reduction in calcium influx in the presence of a test agent indicates that the test agent is useful in reducing food intake and/or treating obesity.

The term "treat" as used herein refers to preventing, ameliorating, controlling, or curing the desired conditions, symptoms or disorders.

An "eating disorder" as used herein refers to a condition or disorder leading to increased food intake, thereby causing the subject to become overweight, characterized by a BMI of 25 or higher. An overweight person having a BMI of 30 or higher is considered obese.

A "physiological disorder" is a disorder leading to an imbalance in bodily functions. Many eating disorders result in, or are associated with, physiological disorders, as described herein. Obesity, for example, is associated with diabetes mellitus, asthma, hypertension, as obesity results in a higher probability for the development of these physiological disorders.

A "subject" is a mammal suffering from an eating disorder or a physiological disorder or condition associated with the eating disorder, such as obesity. The subject may be any kind of mammal, including human, canine, feline, equine, bovine, and rodent. Preferably, the subject is human.

A "calcium channel blocker" is a compound which reduces or inhibits the function of a CNG calcium channel in the olfactory mucosa of a mammal. Preferred calcium channel blocker include diltiazem, verapamil, amlopidine, nimodipine, and isradipine.

The term "modulator" can refer to any natural or synthetic compound that either up- or down-regulates the activity or function of a particular compound, or acts as either an antagonist or an agonist. "Antagonist" refers to a compound, which binds to, and decreases the activity of, a receptor in the presence of an agonist. The term "agonist" refers to a compound, which binds to, and increases the activity of, a receptor as compared with the activity of the receptor in the absence of any agonist.

The term "receptor" refers to a naturally occurring molecule from cells involved in olfactory perception; including but not limited to, odorant binding factors, olfactory receptor neurons and surrounding cells in the nasal mucosa, olfactory nerve, olfactory bulb, and connections to the limbic region of the brain.

The term "signal transduction" can refer to any binding or catalytic event involving receptors and modulators that affect olfactory or gustatory perception.

Calcium Channel Blockers

In olfactory receptor neurons, much of the depolarizing current in response to odors is carried by cationic channels that are directly gated by cyclic AMP. Cyclic nucleotide-gated (CNG) channels comprise a family of proteins, including T-type, N-type, and L-type calcium channels. The CNG channel family has been well studied and molecular modulators have been identified. Examples of known agonists for CNG channels include 8-Br-cGMP, and known antagonists include diltiazem, verapamil and fluoxetine.

Diltiazem (CAS Reg. No. 42399-41-7) is a preferred calcium channel blocker for use in the treatment methods of the invention. This drug belongs to a class of calcium channel blockers that are particularly effective on L-type calcium channels.

Other calcium channel blockers for use according to the methods of the invention include, but are not limited to, verapamil, fluoxetine, nifedipine, nimodipine, amlodipine, felodipine, nicardipine, bepridil and nisoldipine. Particularly preferred of these are verapamil (CAS Reg. No. 52-53-9), amlodipine (CAS Reg. No. 88150-42-9), nimodipine (CAS Reg. No. 66085-59-4), and isradipine (CAS Reg. No. 75695-93-1) which, similarly to diltiazem, target the L-type CNG channels and have a similar effect in the context of the invention.

According to the invention, the calcium channel blockers may be applied as monotherapy or in combination therapy with other therapeutic agents, including, but not limited to, a lipase inhibitor such as Xenical® (Hoffman-La Roche). Such a combination therapy would yield a reduction in food intake using the method of the invention, and a decrease in the metabolization of food by inhibiting lipase activity.

Disorders Associated with Overeating

The methods of the invention are suitable for treating eating disorders, in particular those leading to a person becoming overweight or obese, such as overeating, binge eating, and other conditions. The methods can also be used to treat disorders associated with obesity such as, but not limited to, atherosclerosis, coronary artery disease, hypertension, hypercholesterolemia, diabetes mellitus, gout, osteoarthritis, intertrigo, sleep apnea, hyperlipidemia, hypolipidemia, hypoproteinemia, Pickwickian syndrome, and Cushing syndrome (Rippe, (ed). In: The obesity epidemic: A mandate for a multidisciplinary approach, J Am Dietetic Assoc, 1998;98 (suppl 2):S5-S64).

The compositions of the invention can be used in methods of treating, preventing, inhibiting or alleviating each of the maladies listed above in a mammal, preferably in a human, the methods comprising administering an effective amount of a compound of the invention to a mammal in need thereof. An "effective amount" is an amount sufficient to prevent, inhibit, or alleviate one or more symptoms of the aforementioned conditions, without causing serious side effects or adverse reactions. For example, to treat obesity, an effective amount of a calcium channel blocker is an amount that promotes reduced food or calorie intake.

Formulations

The compositions of the invention may be prepared in a dry or liquid dosage form such as, for example, liquids, suspensions or the like, preferably in unit dosage forms suitable for single administration of precise dosages.

Preferred compositions include a pharmaceutically acceptable carrier or excipient, and one or more of the active compound(s). In addition, the compositions may include other medicinal agents, pharmaceutical agents, carriers, adjuvants, etc. The phrase "pharmaceutically acceptable" refers to additives or compositions that are physiologically tolerable and do not typically produce an allergic or similar untoward reaction, such as gastric upset, dizziness and the like, when administered to an animal, such as a mammal (e.g., a human). The composition or formulation to be administered will, in any event, contain a quantity of one or more of the active compound(s) in an amount effective to alleviate the symptoms of the subject being treated.

Liquified pharmaceutically administrable compositions can, for example, be prepared by dissolving, or dispersing an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known in the art, and described in, e.g., Remington's Pharmaceutical Sciences (Gennaro, A. R., ed., 19th edition, 1995, Mack Publishing Co.) which is herein incorporated by reference.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch. Typical percentages of the active ingredient is 0.001 to 20% by weight, preferably 0.004 to 0.10% by weight.

One or more surfactant may also be included in the formulation. Surfactants should be nontoxic, and preferably soluble in the propellant. Representative of such agents are the esters or partial esters of fatty acids containing from 6 to 22 carbon atoms, such as caproic, octanoic, lauric, palmitic, stearic, linoleic, eleostearic and oleic acids with an aliphatic polyhydric alcohol or its cyclic anhydride such as, for example, ethylene glycol, glycerol, erythritol, arabitol, mannitol, sorbitol, and hexitol anhydrides derived from sorbitol (the sorbitan esters sold under the trademark "Spans") and the polyoxyethylene and polyoxypropylene derivatives of these esters. Mixed esters, such as mixed or natural glycerides, may be employed. The preferred surface-active agents are the oleates orbita, e.g., those sold under the trademarks "Arlacel C" (sorbitan sesquioleate), "Span 80" (sorbitan monoleate) and "Span 85" (sorbitan trioleate). The surfactant may constitute 0.1-20% by weight of the composition, preferably 0.25-5% by weight.

The balance of the composition is ordinarily propellant. Liquefied propellants are typically gases at ambient conditions, and are condensed under pressure. Among suitable liquefied propellants are the lower alkanes containing up to five carbons, such as butane and propane; fluorinated or fluorochlorinated alkanes, such as are sold under the trademark "Freon". Mixtures of the above may also be employed.

In producing the aerosol, a container equipped with a suitable valve is filled with the appropriate propellant, containing the finely divided active ingredient and surfactant. The ingredients are thus maintained at an elevated pressure until released by action of the valve.

Yet another means of administration is topical application of a volatile liquid composition to the skin, preferably facial skin, of an individual. The composition can contain an alcohol such as ethanol or isopropanol. A pleasant odorant may also be included in the composition.

The dosage amount useful to treat, prevent, inhibit or alleviate each of the aforementioned conditions will vary with the severity of the condition to be treated and the route of administration. The dose, and dose frequency will also vary according to age, body weight, response and past medical history of the individual human patient. In generally the recommended daily dose range of diltiazem for the conditions described herein lie within the range of about 0.5 mg to about 10 mg per day, and more preferably within the range of about 1 mg to about 2 mg/day. In managing the patient, is generally preferred that the therapy be initiated at a lower dose and increased if necessary. Dosages for non-human patients, preferably mammals, can be adjusted accordingly by one skilled in the art.

Administration

According to a preferred embodiment, the appropriate modulator molecule is administered directly to the chemoreceptors in the nasal passage. Preferably, although not necessarily, the administration is conducted non-invasively, i.e., without needles.

Liquid dosages may be administered as nose drops or as an aerosol. Alternatively, the active compound can be prepared as a creme or an ointment composition and applied topically within the nasal cavity. In addition, a modulator may be administered as vapor contained in an air puff delivered to the nasal cavity. As another alternative, delivery may occur by controlled release of these agents by encapsulation either in bulk or at a microscopic level using synthetic polymers, such as silicone, and natural polymers such as gelatin and cellulose. The release rate can be controlled by proper choice of the polymeric system used to control the diffusion rate (Langer, R. S. and Peppas, N. A., Biomaterials 2,201, 1981). For example, natural polymers, such as gelatin and cellulose slowly dissolve in a matter of minutes to hours while silicone remains intact for a period of months.

Without being bound to any theory, it is believed that drug action is mediated through binding of the modulators, described herein, to specific receptors displayed by neuroepithelial cells in the nose. Furthermore, the mode of drug action is presumably through the nervous system and not through the circulatory system. Thus, brain function can be affected without consideration of the blood-brain barrier. These methods of treatment provide a direct means of affecting limbic brain responses through the nervous system because there is only one synaptic junction between olfactory receptors and the limbic system of the brain. Because sensory nerves are addressed to a specific location in the brain, this method has a highly specific drug effect, thereby reducing the potential of undesirable side effects.

Screening Methods

As described herein, assays based on identification of modulation of CNG calcium ion channel activity can be used to screen test substances for their potential application in treating eating disorders. Test substances identified as having a fully or partially antagonistic activity against these calcium channels are selected as candidate drugs for further testing in their use for treating eating disorders, obesity, or associated disorders resulting from such conditions.

A "test substance" is a chemically defined compound or mixture of compounds (as in the case of a natural extract or tissue culture supernatant), whose ability to modulate the function of a CNG calcium channel may be evaluated by various assays. A "test substance" is also referred to as a "candidate drug" in the present description.

Test substances may be screened from large libraries of synthetic or natural compounds. Numerous means are currently used for random and directed synthesis of saccharide, peptide, and nucleic acid based compounds. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from, e.g., Pan Laboratories (Bothell, Wash.) or MycoSearch (NC), or are readily producible. Additionally, natural and synthetically produced libraries and compounds are readily modified through conventional chemical, physical, and biochemical means (Blondelle et al., TIBTech 1996, 14:60).

A modulatory effect may be determined by an in vitro method using isolated CG channels and studying binding affinity for the test drug to the channel protein, or by contacting the test drug with cultured cells expressing CNG calcium channels and measuring the effect of CNG channel activity as a result of the contacting. Suitable cells for use in these methods include Odora cells (see, e.g., Liu et al., Talamo Soc. Neurosci. Abstr. 26:1480 (2000)). Odora cells are immortal, grow robustly, and have been shown to express many of the signal transduction components specific to olfactory processes. For example, the influx of calcium in the cells could be measured as a result of contacting the cells with a test drug in the presence of a calcium-sensitive dye (e.g., fura-2AM (Molecular Probes) at 4 $\mu$M), thereby assessing whether the test drug modulates calcium channel activity. The presence of the calcium-sensitive dye in the cells can, for example, be assessed by scanning the cells with a reader capable of detecting the appropriate fluorescence wavelengths. Suitable readers include the FLIPR2 Imaging System (Molecular Probes).

Identification of candidate drugs can be achieved using any suitable assay, including without limitation (i) assays that measure selective binding of test compounds to CNG channels (ii) assays that measure the ability of a test substance to modify (i.e., inhibit) a measurable activity or function of CNG channels and (iii) assays that measure the ability of a substance to modify (i.e., inhibit) the transcriptional activity of sequences derived from the promoter (i.e., regulatory) regions of the CNG channel gene. Animal models can also be used in screening methods to identify candidate drugs.

In a preferred embodiment, candidate drugs are identified by screening in high-throughput assays, including without limitation cell-based or cell-free assays. It will be appreciated by those skilled in the art that different types of assays can be used to detect different types of agents. Several methods of automated assays have been developed in recent years so as to permit screening of tens of thousands of compounds in a short period of time (see, e.g., U.S. Pat. Nos. 5,585,277, 5,679,582, and 6,020,141). Such high-throughput screening methods are particularly preferred.

Selected agents may be modified to enhance efficacy, stability, pharmaceutical compatibility, and the like. Structural identification of an agent may be used to identify, generate, or screen additional agents. For example, where peptide agents are identified, they may be modified in a variety of ways, e.g., to enhance their proteolytic stability.

The present invention will be better understood by reference to the following Examples, which are provided as exemplary of the invention, and not by way of limitation.

EXAMPLE 1

Effect of Intranasal Administration of Diltiazem on Food Intake in Food Deprived Rats This Example shows that Diltiazem administration results in a reduced food intake in an animal model.

Male Sprague-Dawley rats, 150-175 g at the start of the experiments (Charles River Laboratories, Wilmington, Mass.) were housed individually in suspended wire mesh cages; maintained on a reversed-lighting schedule (lights-on at 7 p.m., lights-off at 7 a.m.); and acclimated to our climate controlled animal facility and to the test diets for 7 days prior to experimentation. As the experiments in food-deprived rats were performed during the dark cycle, a dull red light (25 watt) was used to help with placement and weighing of the food jars.

Rats had ad libitum access to tap water and food (Rodent Laboratory Chow No. 5001-pellet form, Purina) on non-testing days. A mush diet, used for experiments on food-deprived animals, and composed of equal parts by weight of ground rodent chow (Purina, # 5001-meal form) and a 4% nutrient agar solution (Teklad Diets) was presented to the animals in glass jars. This agar-based chow diet allows for a more accurate measurement of food intake, and has been shown previously to be sufficient for maintaining normal rat growth.

NB-080 Diltiazem, brand name Cardizem, with a molecular weight of 415 daltons was prepared as a liquid solution in deionized water with the following formulation: Diltiazem HCl 2.17% w/v, NaCl 0.62% w/v, and 1N HCL to adjust to pH 3.5.

On the day of an experiment, food was removed at 7 a.m. prior to lights-off and 4 hours later (11 a.m.) NB-080 was administered intra-nasally, 20 µL/nostril. The drug dosage ranged from 0.02-2 mg/kg of body weight. Control animals were administered 20 µL/nostril of formulation without Diltiazem.

One hour after administration, pre-weighed food jars were introduced into the cage and a sheet of clean white paper placed under each cage to catch any spillage. The amount of food consumed after 1, 2 and 4 hours was determined to the nearest 0.01 g.

As shown in FIG. 1, rats given the drug consumed significantly less food than rats on placebo.

EXAMPLE 2

Dose Range of Diltiazem

A dosing study was performed to determine an optimum concentration for the effect observed in Example 1.

More than 80 rats were used in this feeding study. Diltiazem was administered intra-nasally, 20 µL/nostril. The drug dosage was from 0.02-2 mg/kg of body weight (0.02, 0.2, and 2 mg/kg bodyweight), respectively. Control animals were administered 20 µL/nostril of formulation without diltiazem.

One hour later pre-weighed food jars were introduced into the cage and a sheet of clean white paper placed under each cage to catch any spillage. The amount of food consumed after 1, 2 and 4 hours was determined to the nearest 0.01 g.

Figure 2:
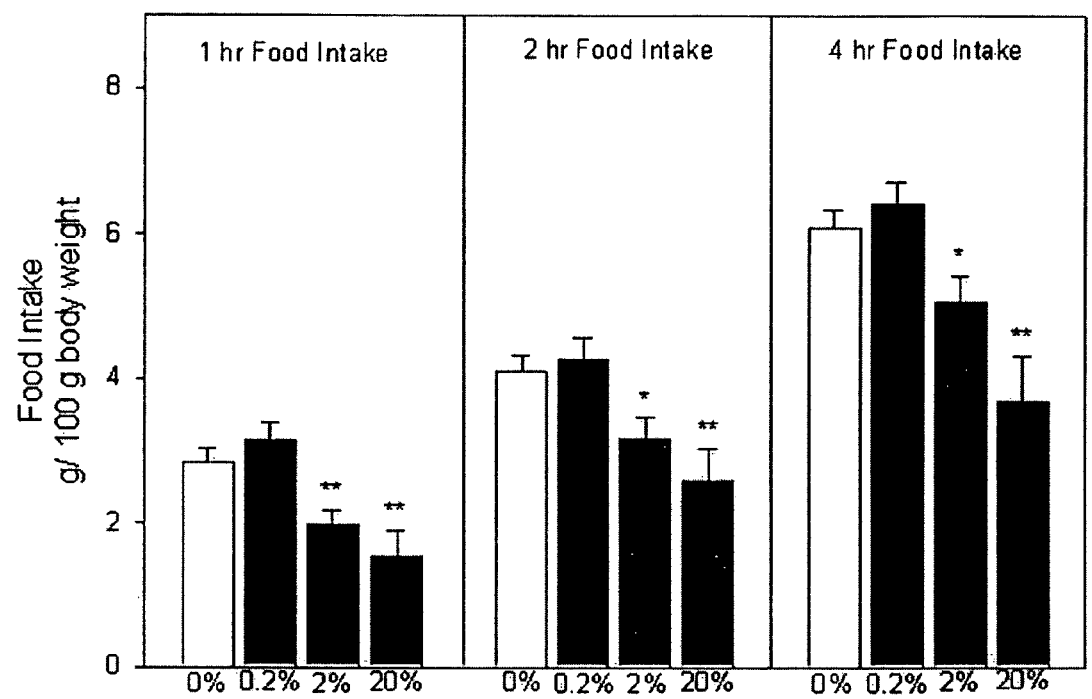
FIG. 2. Effect of intranasal administration of diltiazem on food intake in food deprived rats. Food was given to the animals one hour after drug administration. *=Statistically significant difference from control, $p<0.05$. **=Statistically significant difference from vehicle-treated group (control), $p<0.01$.
Figure 3:
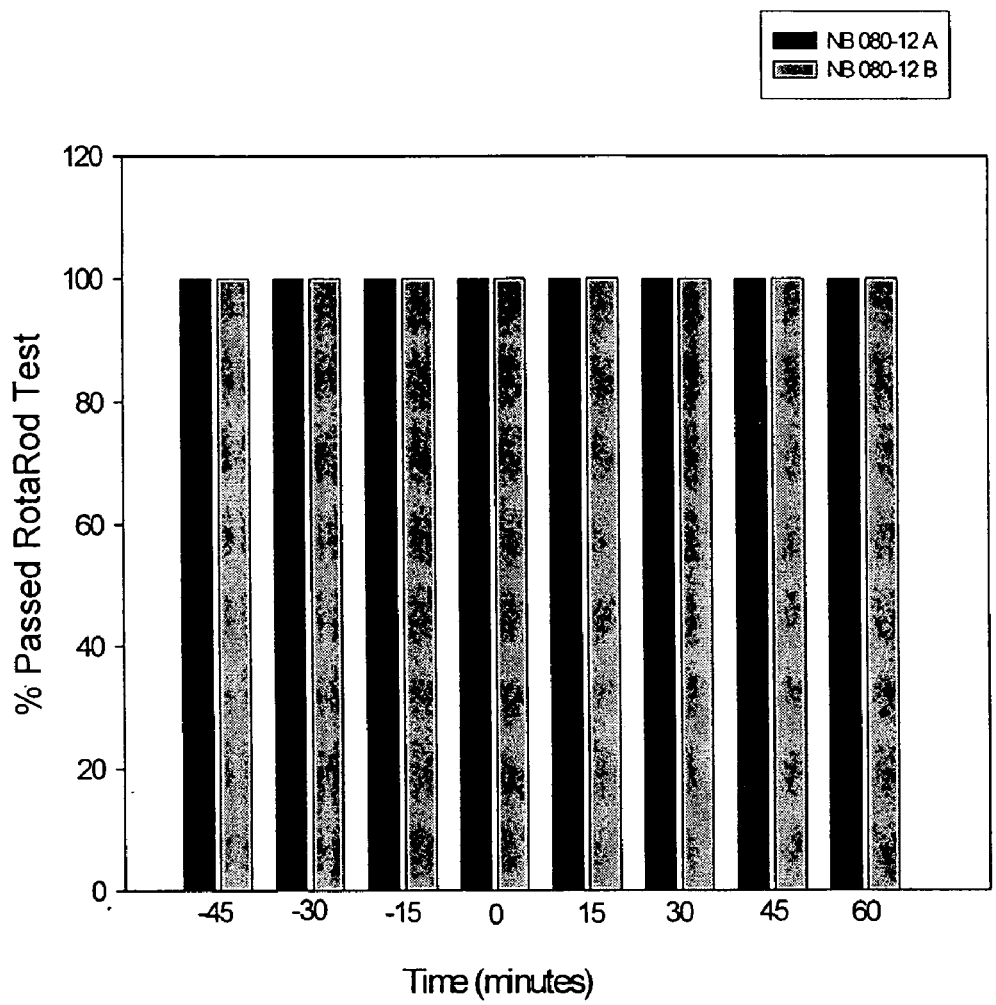
FIG. 3. Effect of intranasal diltiazem on performance of rats in RotaRod test. The drug was administered intranasally (20 µL per nostril) at time 0.
Figure 4:
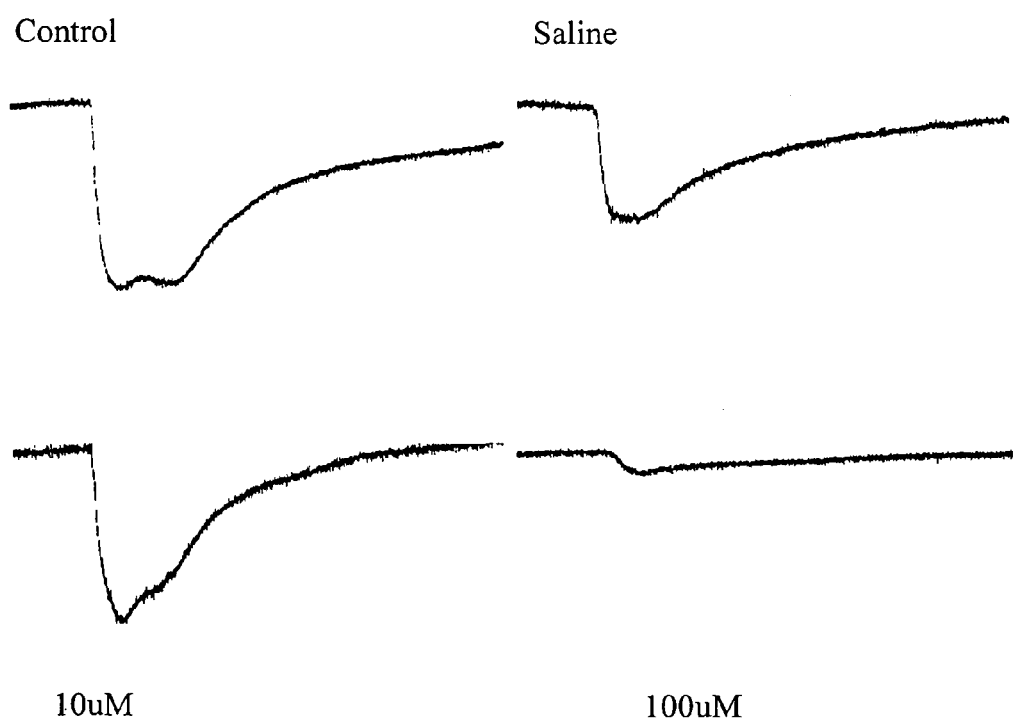
FIG. 4. Effect of intranasal diltiazem on the neuronal activity of olfactory epithelium. The drug was administered intranasally (20 µl/nostril) at 0, 10 µM, and 100 µM concentrations, and neuronal activity was measured using electrophysiological techniques (Example 4).

The result, shown in FIG. 2, were consistent with earlier observations and showed a strong trend toward an optimal dose of 0.2-20% w/v solution of diltiazem.

EXAMPLE 3

Effect of Intranasal Administration of Diltiazem on Animal Performance in Rota-Rod Test This Example reports activity testing of rats administered Diltiazem intranasally.

Two groups of rats (12 rats each) were tested. Each rat went through 8 sessions on the rota-rod: 3 sessions before drug administration (pretest, time −45, −30, and −15 minutes); 1 session immediately after the drug was administered (time 0); and 4 sessions after drug administration (time 15, 30, 45, and 60 minutes).

A speed of 6 rpm was used, and diltiazem was administered, as described above, intra-nasally at 1 mg/kg.

There were no indications of a difference in activity between the drug and vehicle group, thereby showing that the drug did not adversely affect the animals' balance and agility as determined by Rota-Rod testing.

EXAMPLE 4

Diltiazem Electrophysiology Data on Calcium Channel Activity in the Rat Olfactory Epithelium This Example describes measuring the activity of the olfactory nerve in animals with or without prior administration of diltiazem.

A detailed description of the method employed is provided, e.g., by Wong et al. (Neuron 2000: 27: 487-97), and Scott (J Neurosci 2000; 15:4721-31). Briefly, six week old mice were used and each mouse was given 10 µl/nostril of Diltiazem at 10 µM, 100 µM, or saline. It was returned to home cage and euthanized 10 min later for electro-olfactory (EOG) recording. The odorant was Ciltralva at 5 µM. Also included was a "no treatment" control.

Citralva (the test odorant) produced the expected negative potential change in the main olfactory epithelium in the control (saline treated) group, indicating that neuronal activity was present. The lower diltiazem dose had little effect on nerve activity. The olfactory nerve response was, however, blocked by 100 µM diltiazem, showing that diltiazem administration indeed resulted in a blockage of olfactory nerve signaling.

EXAMPLE 5

Effect of Intranasal Administration of Verapamil and Nifedipine on Food Intake in Food Deprived Rats This Example outlines a study on how verapamil and nifedipine administration affects food intake in an animal model.

Male Sprague-Dawley rats, about 150-175 g at the start of the experiments (Charles River Laboratories, Wilmington, Mass.) are housed individually in suspended wire mesh cages; maintained on a reversed-lighting schedule (lights-on at 7 p.m., lights-off at 7 a.m.); and acclimated to climate controlled animal facility and to the test diets for 7 days prior to experimentation. As the experiments in food-deprived rats are performed during the dark cycle, a dull red light (25 watt) is used to help with placement and weighing of the food jars.

Rats have ad libitum access to tap water and food (Rodent Laboratory Chow No. 5001-pellet form, Purina) on non-testing days. A mush diet, used for experiments on food-deprived animals, and composed of equal parts by weight of ground rodent chow (Purina, # 5001-meal form) and a 4% nutrient agar solution (Teklad Diets) is presented to the animals in glass jars. This agar-based chow diet allows for a more accurate measurement of food intake, and has been shown previously to be sufficient for maintaining normal rat growth.

Verapamil and nifedipine are separately prepared as liquid solutions in deionized water with the following formulation: verapamil 2.17% w/v or nifedipine 2.17% w/v; NaCl 0.62% w/v; and 1N HCL to adjust to pH 3.5.

On the day of an experiment, food is removed at 7 a.m. prior to lights-off and 4 hours later (11 a.m.) the drugs are administered intra-nasally, 20 µL/nostril. The drug dosage ranges from 0.02-2 mg/kg of body weight. Control animals are administered 20 µL/nostril of formulation without drug.

One hour after administration, pre-weighed food jars are introduced into the cage and a sheet of clean white paper placed under each cage to catch any spillage. The amount of food consumed after 1, 2 and 4 hours is determined to the nearest 0.01 g.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that values are approximate, and are provided for description.

Patents, patent applications, publications, procedures, and the like are cited throughout this application, the disclosures of which are incorporated herein by reference in their entireties.

What is claimed is:

1. A method of reducing food intake of a subject by inhibiting an L-type cyclic-nucleotide-gated calcium channel, comprising intranasal administration of a pharmaceutical composition comprising an effective amount of an L-type cyclic-nucleotide-gated calcium channel blocker to a subject in need of such treatment.

2. The method of claim 1, wherein the subject suffers from obesity or a physiological disorder associated with obesity.

3. The method of claim 2, wherein the physiological disorder associated with obesity is a member of the group consisting of atherosclerosis, coronary artery disease, hypertension, hypercholesterolemia, diabetes mellitus, gout, osteoarthritis, intertrigo, sleep apnea, hyperlipidemia, hypolipidemia, hypoproteinemia, Pickwickian syndrome, and Cushing syndrome.

4. The method of claim 1, wherein the administration comprises administration to nasal mucosa.

5. The method of claim 1, wherein the pharmaceutical composition is in the form of a liquid or a powder.

6. The method of claim 5, wherein the administration is in the form of inhalation or topical administration.

7. The method of claim 1, wherein the calcium channel blocker is a member of the group consisting of, veraparmil, fluoxetine, nifedipine, nimodipine, amlodipine, felodipine, nicardipine, bepridil and nisoldipine.

8. The method of claim 1, wherein the calcium channel blocker is a member of the group consisting of, verapamil, amlodipine, nimodipine, and israpidine.

9. The method of claim 1, wherein the administration is made from about 0.5 to about 12 hours before food intake.

10. The method of claim 9, wherein the administration is made from about 1 to about 2 hours before food intake.

11. The method of claim 1, comprising intranasal administration of the pharmaceutical composition at least once daily for at least 2 days.

12. The method of claim 11, comprising intranasal administration of the pharmaceutical composition twice daily.

13. A method of treating obesity, comprising intranasal administration of a pharmaceutical composition comprising an effective amount of an L-type cyclic-nucleotide-gated calcium channel blocker to a subject suffering from obesity.

14. The method of claim 13, wherein the administration comprises administration to nasal mucosa.

15. The method of claim 13, wherein the administration is made from about 1 to about 2 hours before food intake.

16. The method of claim 1, wherein the subject is a human.

17. The method of claim 13, wherein the subject is a human.

* * * * *